United States Patent [19]

Shroot et al.

[11] Patent Number: 4,916,136

[45] Date of Patent: Apr. 10, 1990

[54] EICOSATETRAYNOIC ACID AMIDES AND THEIR APPLICATION IN PHARMACY

[75] Inventors: Braham Shroot, Antibes; Christopher Hensby, Biot; Jean Maignan, Tremblay-les-Gones; Gérard Lang, Saint-Gratien; Serge Restle, Aulnay-sous-Bois; Michel Colin, Livry-Gargan, all of France

[73] Assignee: Centre International de Recherches Dermatologioues C.I.R.D., Valbonne, France

[21] Appl. No.: 138,791

[22] Filed: Dec. 28, 1987

[30] Foreign Application Priority Data

Dec. 31, 1986 [FR] France ................. 86 18419

[51] Int. Cl.$^4$ ................. A61K 31/495; A61K 31/535; C07D 295/18; C09F 5/06
[52] U.S. Cl. ................. 514/255; 514/237.5; 514/560; 514/627; 514/62; 514/42; 514/23; 544/386; 544/176; 536/18.7; 260/404; 260/404.5; 260/405.5
[58] Field of Search ............. 560/219; 260/404, 404.5, 260/405.5; 536/18.7; 544/386, 176; 514/62, 237.5, 627

[56] References Cited

U.S. PATENT DOCUMENTS 4,190,669  2/1980  Voorhees et al. ............ 560/219

FOREIGN PATENT DOCUMENTS 104468   4/1984  European Pat. Off. ............ 560/219
161422  11/1985  European Pat. Off. ............ 560/219
0209770  1/1987  European Pat. Off. .

OTHER PUBLICATIONS

Shen et al., The Dev. of an Antiasthma Drug, III, Butterworth Publishers, Kent, Eng., 1981, pp. 315, 316, 317, 331, 332, 333, 334 and 335.

Chemical Abstracts, vol. 97, No. 5, Aug. 2, 1982, No. 38706a, L. A. Yakusheva et al.
Chemical Abstracts, vol. 96, No. 19, May 10, 1962, No. 15 91p, G. I. Myagkova et al.
Chemical Abstracts, vol. 106, No. 19, May 11, 1987, No. 155871r.

*Primary Examiner*—John M. Ford
*Attorney, Agent, or Firm*—Cushman, Darby & Cushman

[57] ABSTRACT

Compound, characterized in that it corresponds to the formula:

$$C_5H_{11}(C\equiv C-CH_2)_4-CH_2CH_2CO\ R \qquad (I)$$

in which R is an amino group of structure

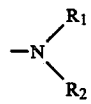

in which $R_1$ and $R_2$, which may be identical or different, denote a hydrogen atom or a linear or branches $C_1$-$C_8$ lower alkyl radical substituted with at least one hydroxyl group, it being possible for this $C_1$-$C_8$ lower alkyl radical to be interrupted by one or more hetero atoms chosen from oxygen, nitrogen or sulphur, $R_1$ and $R_2$ not simultaneously denoting a hydrogen atom and it being possible for $R_1$ and $R_2$ to form, with the nitrogen atom to which they are attached, a heterocycle containing one or more nitrogen, oxygen or sulphur atoms as an additional hetero atom, it being possible for this heterocycle to be optionally substituted with an alkyl or a hydroxyalkyl, and it also being possible for the amino group to be derived from a sugar, and their salts with inorganic or organic acids.

These compounds are used, in particular, in the treatment and prophylaxis of allergic conditions and in the treatment of dermatoses and inflammatory conditions.

17 Claims, No Drawings

EICOSATETRAYNOIC ACID AMIDES AND THEIR APPLICATION IN PHARMACY

The present invention relates to new compounds consisting of eicosatetraynoic acid amides, as well as to their application, on the one hand as therapeutic agents in the treatment or prophylaxis of allergic conditions and in the treatment of dermatoses and inflammatory conditions, and on the other hand in cosmetic compositions.

It is known that a number of substances play an important part in the inflammatory process affecting the skin, such as acne, dermatoses, for example psoriasis, eczema, and the like. These substances, including prostaglandins, hydroxyeicosatetraenoic acids, thromboxanes and leucotrienes, all have a common origin, namely arachidonic acid. (See "VOORHEES-Leuotrienes and Other Lipoxygenase Products in the Pathogenesis and Therapy of Psoriasis and Other Dermatoses" Arch Dermatol, Vol. 119, July 1983, 541–547).

The formation of these substances results chiefly from the release of bound arachidonic acid (bound via an ester bond to lipids present in the epidermis, for example phospholipids), followed by its oxidation by cyclooxygenase and/or lipoxygenases.

For the treatment of skin conditions, either cyclooxygenase inhibitors which prevent prostaglandin formation, such as indomethacin, vitamin E, and the like, or else substances capable of inhibiting lipoxygenases, such as eicosatetraynoic acid, have already been recommended previously.

For the treatment of psoriasis, both 5,8,11,14-eicosatetraynoic acid and 5,8,11-eicosatriynoic acid and their lower alkyl esters have also been recommended (see, in particular, patent US-A-4,190,669).

The applicants have discovered that, surprisingly, particular amides of 5,8,11,14-eicosatetraynoic acid inhibit the enzymatic metabolism of arachidonic acid caused by cyclooxygenase and lipoxygenases. This result is especially unexpected on account of the blocking of the acid group in the form of the amides defined above.

The applicants have found, moreover, that the bioavailability possessed by these compounds is different from that of the corresponding acids, endowing them with improved therapeutic properties.

The subject of the present invention is hence the new 5,8,11,14-eicosatetraynoic acid amides.

Another subject of the invention consists of the pharmaceutical compositions containing such compounds as active substance.

A subject of the invention also consists of the process for preparing these derivatives.

The subject of the invention is, moreover, the use of these compounds in the cosmetics field, in particular in antiacne, antisun or after-sun compositions, or in the treatment of seborrhoeic dermatitis.

Other subjects of the invention will emerge on reading the description and the examples which follow.

The compounds according to the invention are essentially characterized in that they correspond to the formula:

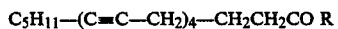

(I)

in which:
R is an amino group of structure

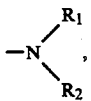

in which $R_1$ and $R_2$ may be identical or different and correspond to a hydrogen atom or a linear or branched $C_1$-$C_8$ lower alkyl radical substituted with at least one hydroxyl group. This $C_1$-$C_8$ lower alkyl radical can be interrupted by one or more hetero atoms chosen from oxygen, nitrogen or sulphur;

$R_1$ and $R_2$ do not simultaneously denote a hydrogen atom;

$R_1$ and $R_2$ can also form, with the nitrogen atom to which they are attached, a heterocycle containing nitrogen, oxygen or sulphur as an additional hetero atom, this heterocycle optionally being substituted with an alkyl or hydroxyalkyl group, the alkyl groups preferably having 1 to 8 carbon atoms; the amino group can also be derived from a sugar; and their salts with inorganic or organic acids.

The especially preferred compounds according to the invention are the compounds corresponding to the formula (I) in which, when $R_1$ corresponds to a hydrogen atom and $R_2$ to an alkyl chain substituted with at least one hydroxyl radical, $R_2$ denotes:

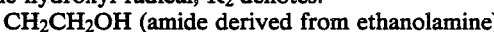
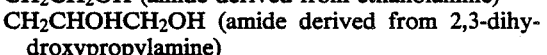
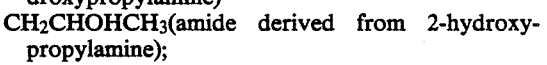

and when the alkyl chain $R_2$ is interrupted by one or more hetero atoms, the preferred meaning is:

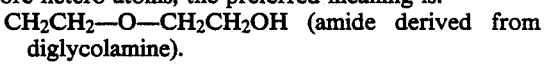

When $R_1$ and $R_2$ are identical, their preferred meaning is:

$CH_2CH_2OH$ (amide derived from diethanolamine).

When $R_1$ and $R_2$ together form a heterocycle, the preferred compounds of the invention are amides derived from morpholine, from piperazine or from 4-(2-hydroxyethyl)piperazine.

When the amino group

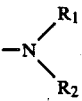

is derived from a sugar, the preferred amino sugar is N-methylglucamine.

The especially preferred compounds of the invention are, in particular:

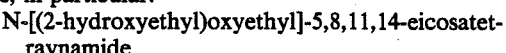
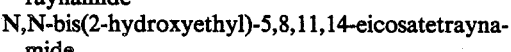
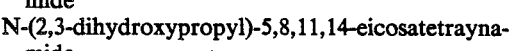
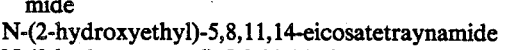
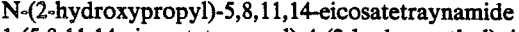
1-(5,8,11,14-eicosatetraynoyl)-4-(2-hydroxyethyl)piperazine and their salts with inorganic or organic acids.

The compounds according to the invention are prepared, generally speaking, from 5,8,11,14-eicosatetraynoic acid. This acid is known per se, in particular from patent US-A-3,033,884.

The subject of the invention is also a new process for preparing this 5,8,11,14-eicosatetraynoic acid, according to the process described in Scheme A below.

This process consists, in a first stage, in treating 1-heptyne (1) with a 1,4-dihalobutyne (2). These two reactants (1) and (2) are known per se. The acetylide of the heptyne (1) is formed by exchange with an alkyl organomagnesium compound such as, preferably, ethylmagnesium bromide.

This acetylide of the heptyne is reacted with the dihalide (2) which is introduced in excess. The 1-halo-2,5-undecadiyne (3) is thereby obtained in good yield.

The main advantage of this process is hence to proceed in one stage from a chain containing 7 carbon atoms to a chain containing 11 carbon atoms having a triple bond at the 2-position and the halogen atom at the 1-position.

The syntheses of this halide hitherto described consisted of chain-elongation reactions using propargyl alcohol. The alcohol thereby synthesized was converted to halide by the action of a phosphorus trihalide, which adversely effected the yield of the process.

The transition from the halide having 11 carbon atoms, of formula (3), to 1-hydroxy-2,5,8-tetradecatriyne (5) is accomplished by the action of the dianion of propargyl alcohol (4). This alcohol of formula (5) is converted, in its turn, to 1-bromo-2,5,8-tetradecatriyne of formula (6), by the action of phosphorus tribromide.

These last two stages are described in patent US-A-3,033,884.

5,8,11,14-Eicosatetrynoic acid is obtained by reacting the dianion of 5-hexynecarboxylic acid, according to a known process, with the 1-bromo-2,5,8-tetradecatriyne of formula (6). The synthesis of this 5-hexynecarboxylic acid is described, in particular, in European Patent Application EP-A-86/109,150.

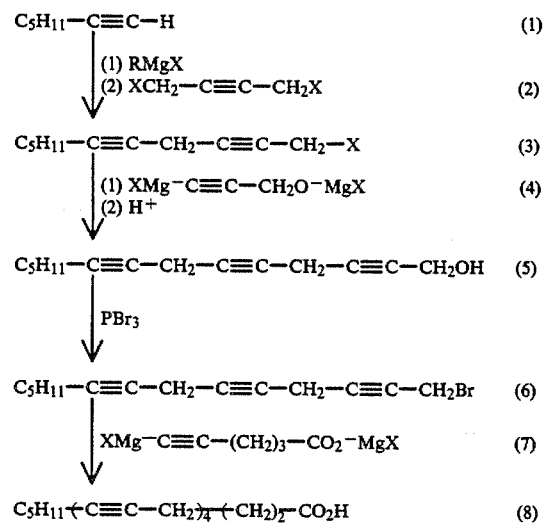

SCHEME A

The amides of formula (I) according to the invention are obtained by reacting an activated form of 5,8,11,14-eicosatetraynoic acid with an amine in an organic solvent.

This activated form of the acid can be either an acid chloride or an anhydride, or alternatively the intermediate formed by adding carbonyldiimidazole (CDI) to a solution of the acid.

This latter reaction is preferably performed in a solvent medium such as dimethylformamide or alternatively in a chlorinated solvent such as dichloromethane or 1,2-dichloroethane. This reaction is illustrated by the following reaction Scheme B:

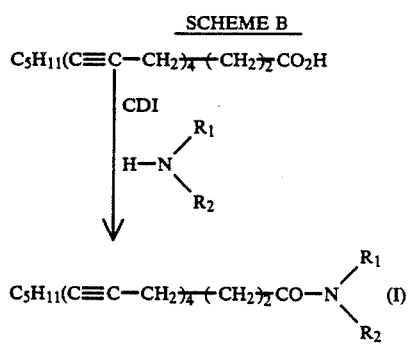

SCHEME B

In the formula (I), $R_1$ and $R_2$ have the meanings stated above.

The compounds of formula (I) according to the invention have especially notable activity with respect to the inhibition of arachidonic acid metabolism, and particularly as regards the lipoxygenases which are at the origin of the formation of leucotrienes and hydroxylated acids which play an important part in the inflammatory process.

The compounds according to the invention may be administered to man or animals by means of compositions containing, in addition, a pharmaceutically acceptable vehicle or diluent. These compositions can also contain, if so desired, other active substances not having an antagonistic effect on the compounds according to the invention.

The compounds according to the invention may be administered systemically or locally.

For enteral administration, the medicinal products may take the form of tablets, gelatin capsules, dragees, syrups, suspensions, solutions, powders, granules, emulsions, suppositories, and the like. For topical application, the pharmaceutical compositions based on compounds according to the invention take, inter alia, the form of ointments, tinctures, creams, pomades, powders, patches, impregnated pads, solutions, lotions, gels, sprays, shampoos or suspensions.

These compositions used topically can be presented either in anhydrous form or in aqueous form, according to the clinical indication.

The pharmaceutical compositions according to the invention can also be administered parenterally and, in particular, intravenously, intramuscularly, intraperitoneally, subcutaneously or intradermally.

For parenteral administration, and more especially injections, the active substance is used in a sterile vehicle such as water. The active substance is either suspended or dissolved in the vehicle.

The compounds according to the invention can also be used in cosmetics, in particular in creams, skin lotions such as antisun products, soothing after-sun products, antiseborrhoeic or antiacne products or shampoos.

The medicinal and cosmetic compositions according to the invention can contain inert or pharmacodynamically or cosmetically active additives, and in particular:

hydrating agents such as thiamorpholinone and its derivatives or urea; antiseborrhoeic agents such as S-carboxymethylcysteine, S-benzylcysteamine and their derivatives, tioxolone; antibiotics such as erythromycin and its esters, neomycin, clindamycin and its derivatives or tetracyclines; agents which interfere with keratinisation such as salicylic acid and α-hydroxycarboxylic acids; agents promoting hair regrowth such as minoxidil (2,4-diamino-6-piperidinopyrimidine 3-oxide) and its derivatives, diazoxide and phenytoin; other steroid and non-steroid anti-inflammatory agents; carotenoids and β-carotene in particular; antipsoriatic agents such as anthralin and its derivatives; and phospholipase $A_2$ inhibitors.

The compositions according to the invention can also contain flavor-improving agents, preservatives, stabilizers, moisture regulators, pH regulators, osmotic pressure modifying agents, emulsifiers, UV-A and UV-B filters, antioxidants such as α-tocopherol, butylated hydroxyanisole or butylated hydroxytoluene, ascorbic acid, local anaesthetics, buffers, and the like.

The compositions according to the invention can also be packaged in delay or sustained-release forms which are known per se. Lastly, they can be introduced into the aqueous phases of liposomes or niosomes.

The active substance according to the invention is present in the pharmaceutical or cosmetic compositions in proportions of between 0.01 and 10% by weight based on the total weight of the composition, preferably between 0.1 and 5% by weight.

In therapeutic application, the treatment is determined by the doctor and can vary according to the age, weight and response of the patient as well as the severity of the symptoms. Dosage is generally between 0.05 and 500 mg/kg/day and preferably 0.5 to 100 mg/kg/day. The treatment period is variable according to the severity of the symptoms, and may extend between 1 and 12 weeks with continuous or discontinuous administration.

In cosmetic application, the compositions according to the invention are chiefly used as antisun products, soothing after-sun products and for the treatment of seborrhoeic dermatitis and/or dermatitis involving acne.

Another subject of the invention consists of the use of the compounds of formula (I) in the preparation of pharmaceutical compositions intended for the treatment or prophylaxis of allergic conditions and in the treatment of acne, dermatoses and inflammatory conditions.

The examples which follow are designed to illustrate the invention without, however, being limiting in nature.

REFERENCE EXAMPLE

Preparation of 5,8,11,14-eicosatetraynoic acid (a) Synthesis of 1-chloro-2,5-undecadiyne 4.17 g (0.17 mol) of magnesium are introduced into a round-bottomed flask equipped with an argon inlet, a condenser and a dropping funnel. The magnesium is covered with THF, a few drops of ethyl bromide are added and the reaction is initiated by heating or by introducing a crystal of iodine. The reaction is maintained at the refluxing point of the THF by the dropwise addition of 14 cm$^3$ of ethyl bromide dissolved in THF, and the mixture is then heated to 70°-80° C. until the magnesium has completely disappeared.

15 g of heptyne (0.156 mol) are added, following the evolution of ethane and maintaining the temperature of 70° C. The reaction is highly exothermic. 1.1 g of copper cyanide are introduced and the mixture is heated to 70° C. for one hour.

The reaction medium is cooled to 50° C. and 43 cm$^3$ (0.44 mol; 2.8 equivalents) of dichlorobutyne are added rapidly. Since the reaction is highly exothermic, the temperature is maintained below 70° C. during the addition by means of a water/ice bath, and the mixture is then heated to 70° C. for approximately 2 hours.

Using GC, it is observed that the heptyne has completely disappeared.

The reaction medium is poured into an ice-cold solution (500 cm$^3$) of ammonium chloride and extracted with ether.

The organic phase is washed, dried over magnesium sulphate and concentrated under reduced pressure.

The expected product is purified by distillation.

The excess dichlorobutyne is removed by distillation at the water pump and the 1-chloro-2,5-undecadiyne is distilled under vacuum using a vane pump.

The expected product distills at 95°-105° C. at 0.01 mm Hg. It is obtained in a 58% yield.

The $^1$H NMR spectrum (80 MHz) is in agreement with the expected structure.

(b) Synthesis of 1-hydroxy-2,5,8-tetradecatriyne 4.8 g of magnesium (0.197 mol) are introduced into a round-bottomed flask equipped with a nitrogen inlet and a dropping funnel. The magnesium is covered with THF, a few drops of ethyl bromide are added and the reaction is initiated by heating or by the addition of an iodine crystal. The reaction is maintained at the refluxing point of the THF by the dropwise addition of 15 cm$^3$ of ethyl bromide (0.203 mol) dissolved in THF, and the mixture is then heated to 70°-80° C. until the magnesium has completely disappeared.

The reaction medium is cooled to 0° C. and 6.2 cm$^3$ (0.105 mol) of propargyl alcohol, distilled and stored over a molecular sieve, are added.

The temperature is maintained at 0° C. for 30 minutes and the mixture is then heated to 70° C. for one hour in order to complete the exchange.

The reaction medium is cooled to 0° C., 0.4 g of copper cyanide is added and the mixture is then heated to 40°-45° C. for approximately one hour.

A solution of 12 g (0.066 mol) of 1-chloro-2,5-undecadiyne in THF is added and the mixture is brought for approximately 20 hours to the refluxing point of the THF.

The reaction is followed by TLC. At the end of the period of heating, traces of starting 1-chloro-2,5-undecadiyne remain.

The reaction medium is poured into 600 cm$^3$ of ammonium chloride solution. The product is extracted with ethyl acetate and the organic phases are washed and dried over magnesium sulphate. A brown oil is obtained by concentration under reduced pressure.

This oil is taken up in hot heptane.

By crystallization in the freezer, 6.8 g (yield: 51%) of a white powder, melting at 26°-27° C., are obtained.

the $^1$H NMR spectrum is in agreement with the expected structure.

(c) Synthesis of 1-bromo-2,5,8-tetradecatriyne 6 g of 1-hydroxy-2,5,8-tetradecatriyne prepared above, dissolved in 30 cm$^3$ of ethyl ether, are introduced into a round-bottomed flask equipped with an argon inlet. 0.05 cm$^3$ of pyridine is added and 1 cm$^3$ of phosphorus tribromide is added dropwise, and the mixture is then brought to reflux for 3 hours.

After it has been verified by TLC that the reaction is complete, the reaction medium is poured into ice-cold water and the expected product extracted with ether. The organic phases are washed with dilute sodium carbonate solution and then with water. They are dried over magnesium sulphate and concentrated under reduced pressure.

8 g of a brown oil are recovered, whose $^1$H NMR spectrum (80 MHz) corresponds to the expected structure and which will be used without further treatment for the subsequent reactions.

(d) Synthesis of 5,8,11,14-eicosatetraynoic acid 3.8 g (0.156 mol) of magnesium are introduced into a round-bottomed flask equipped with an argon inlet, a condenser and a dropping funnel.

The magnesium is covered with THF and the Grignard reagent formed by adding 13 cm$^3$ (0.172 mol) of ethyl bromide.

Heating is maintained until the magnesium has completely disappeared.

The reaction medium is cooled to 0° C. and 7.7 g of 5-hexynecarboxylic acid, dissolved in THF, are introduced dropwise.

The temperature is allowed to rise to 25° C. during 2 hours. 0.6 g of copper cyanide is added, stirring is maintained for 2 hours at room temperature and 8 g (0.03 mol) of 1-bromo-2,5,8-tetradecatriyne obtained above, dissolved in THF, are then added.

The mixture is heated for approximately 20 hours at the refluxing point of the THF. Using TLC, it is observed that the reaction is not proceeding further.

The reaction medium is poured into dilute hydrochloric acid solution in ice. The product is extracted with ethyl acetate.

The organic phases are washed with sodium hydrogen carbonate solution to remove the excess 5-hexynecarboxylic acid. The organic phase is washed again with water and the dried.

It is concentrated under reduced pressure, and the crude product thereby obtained is then recrystallized in a minimum amount of methanol.

1.5 g of pale cream crystals is recovered, whose melting point is 78°–80° C. and which appear to be hygroscopic.

The $^1$H NMR and IR spectra are in agreement with the expected structure.

Elementary analysis: $C_{20}H_{24}O_2$

|  | C | H | O |
|---|---|---|---|
| Theoretical value | 81.04 | 8.16 | 10.72 |
| Value found | 77.96 | 8.25 | 13.73 |
| Theoretical value with ⅓ H$_2$O | 77.95 | 8.21 | 13.85 |

PREPARATION EXAMPLE 1

Synthesis of
N-[(2-hydroxyethyl)oxyethyl]-5,8,11,14-eicosatetraynamide 1.1 g of carbonyldiimidazole are added to a solution, outgassed with argon, of 1.5 g of 5,8,11,14-eicosatetraynoic acid (5 mmol) in 30 cm$^3$ of anhydrous DMF, and the mixture is heated to 50° C. for 1 hour 30 minutes.

The solution is cooled to 0° C. and 1.05 g (0.01 mol) of (2-hydroxyethyl)oxyethylamine, dissolved in 10 cm$^3$ of DMF, is then added.

The mixture is allowed to return to room temperature during 2 hours, and then, after the disappearance of the starting acid has been verified using TLC, the reaction medium is poured into dilute ammonium chloride solution and the product extracted with ethyl acetate. The organic phases are washed with water. They are dried and concentrated under reduced pressure.

The crude reaction product is crystallized in heptane.

By recrystallization in diisopropyl ether, 1.1 g of a white powder is obtained, whose melting point is 68°–69° C.

The $^{13}$C NMR and IR spectra are in agreement with the expected structure.

Elementary analysis: $C_{24}H_{33}NO_3$

|  | C | H | N | O |
|---|---|---|---|---|
| Theoretical value | 75.16 | 8.67 | 3.65 | 12.51 |
| Value found | 74.60 | 8.73 | 3.81 | 13.23 |

PREPARATION EXAMPLE 2

Synthesis of
1-(5,8,11,14-eicosatetraynoyl)-4-(2-hydroxyethyl)piperazine 1.1 g of carbonyldiimidazole are added to a solution, outgassed with argon, of 1.5 g of 5,8,11,14-eicosatetraynoic acid (5 mmol) in 30 cm$^3$ of anhydrous DMF, and the mixture is heated to 50° C. for 1 hour 30 minutes.

The solution is cooled to 0° C. and 1.3 g of (2-hydroxyethyl)piperazine (0.01 mol), dissolved in 10 cm$^3$ of DMF, is then added.

The mixture is allowed to return to room temperature during 2 hours, and then, after the disappearance of the starting acid has been verified using TLC, the reaction medium is poured into dilute ammonium chloride solution. The product is extracted with diisopropyl ether and the organic phases are washed copiously with water to remove the excess (2-hydroxyethyl)piperazine. They are dried and concentrated under reduced pressure.

1 g of a brown oil is recovered, whose $^{13}$C NMR and IR spectra are in agreement with the expected structure.

Elementary analysis: $C_{26}H_{28}N_2O_2$

|  | C | H | N | O |
|---|---|---|---|---|
| Theoretical value | 77.96 | 7.04 | 6.99 | 7.99 |
| Value found | 74.65 | 8.54 | 6.94 | 9.99 |
| Theoretical value with ⅓ H$_2$O | 75.18 | 7.20 | 6.78 | 10.64 |

PREPARATION EXAMPLE 3

Synthesis of
N-(2-hydroxyethyl)-5,8,11,14-eicosatetraynamide 360 mg of carbonyldiimidazole are added to a solution, outgassed with argon, of 500 mg of 5,8,11,14-eicosatetraynoic acid (1.7 mmol) in 20 cm$^3$ of anhydrous 1,2-dichloroethane while the solution is maintained at 15° C. for approximately 1 hour.

The solution is cooled to 0° C. and 200 mg of ethanolamine, dissolved in 1,2-dichloroethane, are then added.

The mixture is left overnight at room temperature, and then, after the disappearance of the starting acid has been verified using TLC, the reaction medium is poured into dilute hydrochloric acid solution.

The product is extracted with dichloromethane and the organic phases are washed copiously with water to remove the excess ethanolamine. They are dried and concentrated under reduced pressure.

250 mg of a white powder are recovered, which is recrystallized in acetonitrile and whose melting point is 93°–94° C.

The $^1$H NMR (80 MHz) and IR spectra correspond to the expected structure.

PREPARATION EXAMPLE 4

Synthesis of N-(2,3-dihydroxypropyl)-5,8,11,14-eicosatetraynamide 360 mg of carbonyldiimidazole are added to a solution, outgassed with argon, of 500 mg of 5,8,11,14-eicosatetraynoic acid (1.7 mmol) in 20 cm$^3$ of anhydrous 1,2-dichloroethane while the solution is maintained at 15° C. for approximately one hour.

The solution is cooled to 0° C. and 310 mg of 3-amino-1,2-propanediol, dissolved in 1,2-dichloroethane, are then added. The mixture is left overnight at room temperature, and then, after the disappearance of the starting acid has been verified using TLC, the reaction medium is poured into dilut hydrochloric acid solution.

The product is extracted with dichloromethane and the organic phases are washed copiously with water to remove the excess 3-amino-1,2-propanediol. They are dried and concentrated under reduced pressure.

200 mg of a white powder are recovered, which is purified by chromatography on silica gel (eluent: chloroform/ethylacetate/methanol) and whose melting point is 95°–96° C.

The $^1$H NMR (80 MHz) and IR spectra are in agreement with the expected structure.

The examples which follow are designed to illustrate compositions according to the invention.

EXAMPLE 1

The following composition is prepared:

| | |
|---|---|
| N-(2-hydroxyethyl)-5,8,11,14-eicosatetraynamide | 5.0 g |
| Micronized polyethylene | 10.0 g |
| Isopropyl myristate qs | 100.0 g |

This composition takes the form of a hydrophobic ointment intended for topical application. Good results are also obtained by replacing the N-(2-hydroxyethyl)-5,8,11,14-eicosatetraynamide in this ointment by N-(2,3-dihydroxypropyl)-5,8,11,14-eicosatetraynamide or by N-[(2-hydroxyethyl)oxyethyl]-5,8,11,14-eicosatetraynamide.

EXAMPLE 2

The following composition is prepared:

| | |
|---|---|
| N-(2,3-dihydroxypropyl)-5,8,11,14-eicosatetraynamide | 1.0 g |
| Triglycerides of capric, caprylic and stearic acids | 40.0 g |
| Triglycerides of capric and caprylic acids | 30.0 g |
| Vaseline | 20.0 g |
| Liquid paraffin qs | 100.0 g |

This composition takes the form of a hydrophobic ointment intended for topical application.

EXAMPLE 3

The following composition is prepared:

| | |
|---|---|
| 1-(5,8,11,14-Eicosatetraynoyl)-4-(2-hydroxyethyl)piperazine | 0.5 g |
| Cetyl alcohol | 6.4 g |
| Cetyl alcohol oxyethylenated with 20 mol of ethylene oxide | 2.1 g |
| Glycerol monostearate | 2.0 g |
| Triglycerides of capric and caprylic acids | 15.0 g |
| Propylene glycol | 10.0 g |
| Water qs | 100.0 g |

This composition takes the form of a cream intended for topical application.

EXAMPLE 4

The following lotion is prepared:

| | |
|---|---|
| N-(2,3-dihydroxypropyl)-5,8,11,14-eicosatetraynamide | 0.1 g |
| Ethanol | 50.0 g |
| Propylene glycol qs | 100.0 g |

This lotion is used for topical application.

The compositions of Examples 1 to 4 above are all manufactured and stored in an inert atmosphere and shielded from the light.

EXAMPLE 5

The following composition is prepared:

| | |
|---|---|
| N-(2,3-dihydroxypropyl)-5,8,11,14-eicosatetraynamide | 0.01 g |
| Absolute ethanol | 1.0 ml |
| Flavoring qs, preservative qs, | |
| Glycerol qs | 5.0 ml | which is introduced into a 5-ml brown glass ampoule and intended for oral use in the form of a solution to be taken by mouth.

EXAMPLE 6

A 350-mg gelatin capsule is prepared containing a powder having the following composition:

| | |
|---|---|
| N-[(2-hydroxyethyl)oxyethyl]-5,8,11,14-eicosatetraynamide | 0.025 g |
| Microcrystalline cellulose | 0.020 g |
| Maize starch | 0.100 g |
| Colloidal silica | 0.020 g |
| Magnesium stearate | 0.185 g |

EXAMPLE 7

Granules having the following composition are prepared:

| | |
|---|---|
| 1-(5,8,11,14-Eicosatetraynoyl)-4-(2-hydroxyethyl)piperazine | 0.500 g |
| Methyl cellulose | 0.020 g |
| Purified water | 0.400 g |
| Sucrose | 1.480 g |

The paste obtained by mixing the four constituents is granulated by the wet method and dried.

The granules are presented in 2-g sachets, the recommended dosage being four sachets per day.

We claim:

1. A compound having the formula:

$$C_5H_{11}(C\equiv C-CH_2)_4-CH_2CH_2COR \qquad (I)$$

wherein

R is $N\begin{smallmatrix}R_1\\R_2\end{smallmatrix}$ wherein $R_1$ and $R_2$, each independently, represent hydrogen, linear or branched lower alkyl having 1–8 carbon atoms substituted with at least one hydroxy group, optionally interrupted by one heteroatom selected from oxygen, nitrogen or sulfur, with the proviso that $R_1$ and $R_2$ are not hydrogen simultaneously, or $R_1$ and $R_2$ together with the nitrogen atom to which they are attached form a heterocycle selected from morpholino, piperazino and 4-(2-hydroxyethyl) piperazino, or said $-N\begin{smallmatrix}R_1\\R_2\end{smallmatrix}$ represents N-methylglucamine, and
an inorganic or organic salt of said compound.

2. The compound of claim 1 wherein $R_1$ is hydrogen and $R_2$ is $-CH_2CH_2-O-CH_2CH_2OH$, $-CH_2CH_2OH$, $-CH_2-CHOHCH_3$ or $-CH_2CHOHCH_2OH$.

3. The compound of claim 2 which is N-[(2-hydroxyethyl)oxyethyl]-5,8,11,14-eicosatetraynamide.

4. The compound of claim 2 which is N-(2-hydroxyethyl)-5,8,11,14-eicosatetraynamide.

5. The compound of claim 2 which is N-(2,3-dihydroxypropyl)-5,8,11,14-eicosatetraynamide.

6. The compound of claim 1 which is 1-(5,8,11,14-eicosatetraynoyl)-4-(2-hydroxyethyl)piperazine.

7. A pharmaceutical composition for the treatment or prophylaxis of allergic conditions by inhibiting the enzymatic metabolism of arachidonic acid comprising, in a pharmaceutically acceptable carrier, the compound of formula I of claim 1 present in an amount ranging from 0.01 to 10 weight percent based on the total weight of said composition.

8. A pharmaceutical composition for the treatment of acne, dermatoses and inflammatory conditions comprising, in a pharmaceutically acceptable carrier, in an amount effective to treat said acne, dermatoses and inflammatory conditions, the compound of formula I of claim 1.

9. The pharmaceutical composition of claim 8 wherein said compound of formula I is present in an amount ranging from 0.01 to 10 percent by weight based on the total weight of said composition.

10. The pharmaceutical composition of claim 8 wherein said compound of formula I is present in an amount ranging from 0.1 to 5 percent by weight based on the total weight of said composition.

11. The pharmaceutical composition of claim 8, for topical administration, in the form of a cream, a tincture, an ointment, a pomade, a powder, a patch, an impregnated pad, a solution, a gel, a lotion, a spray or a suspension.

12. The pharmaceutical composition of claim 8 for parenteral administration, wherein said compound of formula I is suspended or dissolved in water.

13. The pharmaceutical composition of claim 8, for enteral administration, in the form of a tablet, a gelatin capsule, a dragee, a syrup, a suspension, a solution, a powder, a granule or an emulsion.

14. A process for the treatment and prophylaxis of an allergic condition and for the treatment of dermatoses and an inflammatory condition, said process comprising administering to a mammalian an effective amount of, to treat said allergic condition, said dermatoses or said inflammatory condition, said compound of claim 1.

15. The process of claim 14 wherein said compound is administered at a daily dosage of 0.05 to 100 mg/kg of said mammalian.

16. The process of claim 14 wherein said compound is administered at a daily dosage of 0.5 to 50 mg/kg of said mammalian.

17. A process for preparing eicosatetraynoic acid comprising
(a) treating 1-heptyne having the formula $$C_5H_{11}-C\equiv C-H \qquad (1)$$

with a strong base to form the corresponding acetylide,
(b) reacting the said acetylide from (a) with 1,4-dihalo-2-butyne having the formula $$XCH_2-C\equiv C-CH_2X \qquad (2)$$

to produce 1-halo-2,5-undecadiyne of the formula $$C_5H_{11}-C\equiv CH_2-C\equiv C-CH_2X \qquad (3),$$

(c) reacting said 1-halo-2,5-undecadiyne (3) with the dianion of propargyl alcohol,
(d) brominating the product resulting from (c) with phosphorus tribromide to obtain 1-bromo-2,5,8-tetradecatriyne of the formula $$C_5H_{11}-C\equiv C-CH_2-C\equiv C-CH_2-C\equiv C-CH_2-Br \qquad (6)$$

and
(e) reacting said 1-bromo-2,5,8-tetradecatriyne from (d) with the dianion of 5-hexynecarboxylic acid.

* * * * *